United States Patent [19]

Wu

[11] 4,219,683

[45] Aug. 26, 1980

[54] ISOMERIZATION OF UNSATURATED ALCOHOLS

[75] Inventor: Yulin Wu, Bartlesville, Okla.

[73] Assignee: Phillips Petroleum Company, Bartlesville, Okla.

[21] Appl. No.: 945,670

[22] Filed: Sep. 25, 1978

[51] Int. Cl.$^2$ ...................... C07C 33/02; C07C 33/06
[52] U.S. Cl. ................................... 568/906; 568/812; 568/813
[58] Field of Search ................ 568/906, 903, 812, 813

[56] References Cited

U.S. PATENT DOCUMENTS

| | | | |
|---|---|---|---|
| 1,963,998 | 6/1934 | Larchar | 568/903 |
| 2,837,577 | 6/1958 | Plaser et al. | 568/906 |
| 3,355,505 | 11/1967 | Tedeschi | 568/906 |
| 3,696,155 | 10/1972 | Mueller et al. | 568/906 |
| 3,697,580 | 10/1972 | Overwein et al. | 568/906 |

*Primary Examiner*—Joseph E. Evans

[57] ABSTRACT

Olefinically unsaturated compounds, such as nitriles, alcohols, esters, ethers and the like are isomerized to other unsaturated compounds in the presence of a palladium-thorium oxide catalyst and hydrogen.

9 Claims, No Drawings

ISOMERIZATION OF UNSATURATED ALCOHOLS

This invention relates to the isomerization of olefinically unsaturated compound to isomeric unsaturated compound. In accordance with one aspect, this invention relates to the isomerization of olefinically unsaturated compounds such as nitriles, alcohols, esters, ethers and the like in the presence of a palladium-thorium oxide catalyst. In accordance with a further aspect, 3-methyl-3-buten-1-ol is isomerized to 3-methyl-2-buten-1-ol in high yield in the presence of a palladium-thorium oxide catalyst and hydrogen.

I. Background

The isomerization of olefinically unsaturated alcohols to isomeric unsaturated alcohols in the presence of a palladium metal catalyst is known. For example, in U.S. Pat. No. 3,697,580, 2-methylbutene-1-ol-4 (or 3-methyl-3-buten-1-ol) is isomerized to 2-methylbuten-2-ol-4 (or 3-methyl-2-buten-1-ol) in the presence of palladium of carbon. However, the use of isomerization catalysts such as Pd/C has several drawbacks. At isomerization temperatures of about 100° to 150° C., the rate of isomerization of unsaturated alcohols in the presence of catalysts such as Pd/C is relatively low. In addition, the Pd/C catalysts are difficult to regenerate following extended usage due to degradation during burn-off in the presence of oxygen.

The present invention provides a palladium catalyst on a thorium oxide support for the isomerization of olefinically unsaturated alcohols to other unsaturated alcohols with significantly higher rates of isomerization and better regenerability than the prior art catalysts.

Accordingly, an object of this invention is to provide an improved process for isomerization of olefinically unsaturated compounds.

Another object of this invention is to provide an improved catalyst for the isomerization of olefinically unsaturated compounds.

Other objects, aspects, as well as the several advantages of the invention will be apparent to those skilled in the art upon reading the specification and the appended claims.

In accordance with the invention, unsaturated compounds are isomerized to other unsaturated compounds in the presence of a palladium-thorium oxide catalyst and hydrogen.

More specifically, in accordance with the invention, unsaturated alcohols are isomerized to other unsaturated alcohols in the presence of a palladium-thorium oxide catalyst and hydrogen.

In accordance with one specific embodiment, 3-methyl-3-buten-1-ol is isomerized to 3-methyl-2-buten-1-ol in high yield in the presence of a palladium-thorium oxide catalyst and hydrogen.

II. Scope of Reactant

The present invention is applicable to the isomerization of any olefinically unsaturated compound capable of being isomerized to a corresponding isomer but generally it is applicable to unsaturated materials containing from 4 to about 30 carbon atoms per molecule which can be represented by the following general formulas:

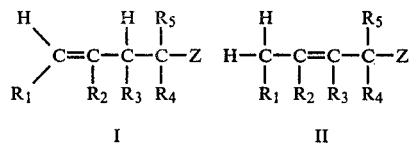

wherein each of $R_1$, $R_2$, $R_3$, $R_4$, and $R_5$ is selected from a group consisting of hydrogen, an alkyl radical containing from 1 to 10 carbon atoms per molecule, or an aryl or substituted aryl radical containing from 6 to 14 carbon atoms per molecule with the substituents being one or more or a mixture of alkyl or cycloalkyl groups containing 1 to 10 carbon atoms, halogens, or alkoxy groups containing 1 to about 10 carbon atoms per group. In addition, any two of $R_1$, $R_2$, $R_3$, or $R_4$ can be taken together to form an alkylene radical thus forming a cyclic system with the ring preferably containing from 5 to 7 carbon atoms. Z can be —CN or —OR$_6$ wherein $R_6$ can be selected from the groups described above for $R_1$ through $R_5$ and the group

wherein $R_7$ is selected from the groups described above for $R_1$ through $R_5$. Therefore, I and II can be an olefinically unsaturated nitriles, alcohols, esters, or ethers.

The currently preferred starting materials for the isomerization reaction of this invention are those in which Z is the —OH group, $R_1$, $R_3$, $R_4$, and $R_5$ are hydrogen and $R_2$ is an alkyl radical containing from 1 to 10 carbon atoms per molecule. The compounds of formula I can be prepared by the reaction of formaldehyde with olefins such as isobutylene as described, for example, in U.S. Pat. Nos. 3,956,407, 3,960,972, and 3,960,973. The compounds of formula II can be prepared by several methods including the selective hydrogenation of the corresponding unsaturated aldehydes e.g., Chem. Abst., 85, 177695 m (1976).

Specific examples of starting materials of the general formula I for the isomerization reaction of this invention include 3-buten-1-ol, 3-methyl-3-buten-1-ol, 3-penten-1-ol, 3,4-dimethyl-4-penten-2-ol, 2-ethyl-3-buten-1-ol, 1-decen-4-ol, 1-methyl-3-methylenecyclohexanol, 2-ethyl-3-methylenecyclopentanol, 3-methylenecyclohexanol, 3-methylenecycloheptanol, 3-phenyl-3-buten-1-ol, the analogous methyl, ethyl, cyclohexyl, phenyl, p-chlorophenyl, or α-naphthyl ethers, the analogous acetic, cyclohexanecarboxylic, benzoic, or α-naphthoic esters, and 4-pentenenitrile.

Specific examples of starting materials of the general formula II for the isomerization reaction of this invention include 2-buten-1-ol, 3-methyl-2-buten-1-ol, 2-penten-1-ol, 3,4-dimethyl-3-penten-2-ol, 2-ethyl-2-buten-1-ol, 1,3-dimethyl-2-cyclohexenol, 2-decen-4-ol, 2-ethyl-3-methyl-2-cyclopentenol, 3-methyl-2-cyclopentenol, 3-methyl-2-cyclohexenol, 3-methyl-2-cycloheptenol, 3-phenyl-2-buten-1-ol, the analogous methyl, ethyl, cyclohexyl, phenyl, p-chlorophenyl, or α-naphthyl ethers, the analogous acetic, cyclohexanecarboxylic, benzoic, or α-naphthoic esters, and 3-pentenenitrile.

The starting materials for the isomerization reaction of this invention can be compounds of formula I, formula II, or mixtures of compounds of formula I and compounds of formula II. Generally, the mixture of compounds of formulas I and II will have the same $R_1$, $R_2$, $R_3$, $R_4$, $R_5$, and Z radicals to avoid product separation difficulties.

III. Reaction Product

The catalytic isomerization of compounds of general formula I or of compounds of general formula II will yield a mixture of compounds I and II from which the desired isomer can be separated and the other isomer can be recycled to the isomerization step. This isomerization reaction can be illustrated by the following example.

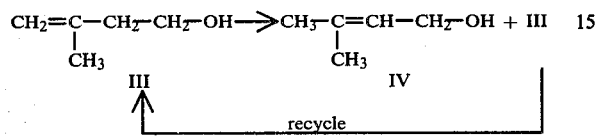

3-Methyl-3-buten-1-ol (III) can be isomerized in the presence of the catalyst of this invention to yield a mixture of 3-methyl-2-buten-1-ol (IV) and III. This mixture can be separated, e.g. by fractional distillation, to obtain IV and to recover III for recycle to the isomerization stage. Likewise, IV can be isomerized to a mixture of III and IV from which III can be separated as a product and the IV can be recovered for recycling to the isomerization stage.

Suitable mixtures, i.e., non-equilibrium mixtures, of isomeric compounds of general formulas I and II can also be employed in the process of this invention. As an example, a mixture containing predominantly 3-methyl-3-buten-1-ol (III), e.g., 98%, along with 3-methyl-2-buten-1-ol (IV), e.g., 2%, can be isomerized in the presence of the catalyst of this invention to give a mixture enriched in IV from which the IV can be separated and the III recycled to the isomerization stage.

IV. Scope of Catalyst

The catalyst which is utilized according to the present invention to provide an increase in the rate of isomerization of compounds of the general formulas I and/or II comprises palladium on a thorium oxide support. As will be shown in the examples, the use of the thorium oxide support is the feature of this invention that provides the significant increase in isomerization rate.

The thorium oxide support can be utilized in the form of powders, pellets, granules, pills, spheres, extrudates, and the like, and mixtures thereof. Although the support can be pure thorium oxide, for economic reasons it can also contain other materials. Small quantities of the compounds of other rare earth elements such as lanthanum, cerium, neodymium, and the like are frequently present in thorium compounds and can be present in the thorium oxide in levels of up to about 10 weight % or even as much as 25 weight % without significantly adversely affecting the isomerization rate.

The palladium on thorium oxide isomerization catalyst can be prepared by any of the methods well known in the art. For example, the supported catalyst can be prepared by dry mixing the components or by impregnating the thorium oxide support with a solution or dispersion of palladium in elemental form or in the form of reducible compounds of palladium. Examples of suitable reducible compounds of palladium (II) or (IV) include the bromides, chlorides, nitrates, oxides, acetates, and the like, and mixtures thereof. The impregnated support can be reduced in the presence of hydrogen.

The amount of palladium metal present in the supported catalyst will be broadly from about 0.1 to about 30 and preferably from about 0.5 to about 10 weight % metal with the percentages being based on the weight of the support.

In the event the palladium-thorium oxide catalyst loses activity, it can be readily regenerated by contacting with a reducing agent such as hydrogen at an elevated temperature in the range of about 500° F. to about 800° F. for a period of time sufficient to restore catalyst activity.

V. Isomerization Conditions

In batch reactions using the isomerization reaction of this invention the amount of supported catalyst utilized is broadly from about 0.1 to about 60% and preferably from about 0.5 to about 50% by weight based on the weight of the starting material.

The isomerization reaction is carried out in the presence of hydrogen. The hydrogen is generally present initially at a pressure of about 0 to about 100 psig and preferably from about 0.5 to about 50 psig. Various gases substantially inert under the reaction conditions such as nitrogen or argon can be present along with the hydrogen, but oxygen is preferably excluded from the reaction vessel.

The temperature utilized in the isomerization reaction can range from about 0° to about 200° C., but the advantages of this invention are obtained within a temperature range of about 40° to about 150° C.

The time utilized will depend on the amount of catalyst and the desired degree of conversion of the starting material. However, the reaction time will generally range from a few minutes to several hours. Since the catalyst of this invention provides an increase in reaction rate at reaction temperatures above about 40° C. compared with prior art catalysts, the amount of reaction time to achieve a certain degree of conversion will be less than in prior art processes.

Although the isomerization reaction of this invention is normally carried out in the absence of an added diluent, a reaction diluent that is substantially inert under the reaction conditions can be employed. Compounds such as saturated alcohols containing 1 to 12 carbon atoms per molecule, hydrocarbons such as alkanes, cycloalkanes, aromatics, and alkylsubstituted aromatics containing 4 to 20 carbon atoms per molecule, or saturated ethers containing 4 to 20 carbon atoms per molecule can be utilized as diluents.

The quantities of said diluents can range from about 1/20 to about 20/1 volumes of diluent to volumes of unsaturated alcohol reactant.

Intimate contact of the reactant and catalyst is expected to be of benefit in the isomerization reaction and conventional means of good mixing by stirring, shaking, and the like can be employed as taught in the prior art.

The isomerization reaction of this invention can be carried out in either a batch or a continuous manner. The continuous run can be carried out at any suitable liquid hourly space velocity (LHSV). However, the LHSV will generally be within the range of from about 0.1 to about 10, preferably from about 0.5 to about 5 volumes of feed stream plus diluent if present per volume of supported catalyst.

VI. Workup of Reaction Product

At the conclusion of the isomerization reaction of this invention, the reaction product mixture can be processed through conventional separation means to recover the catalyst, any unchanged starting material, any diluent that was present, and the isomerization product. Generally the reaction product mixture is filtered to remove the catalyst and then fractionally distilled to separate the diluent, if present, and any unreacted starting material for recycle to the isomerization zone and the isomerization product.

Other separation techniques such as an extractive distillation with a suitable solvent can also be employed for the separation of starting material and product.

VII. Product Utility

The compounds prepared by the process of this invention are useful as starting materials for the preparation of agricultural chemicals and as blending agents for motor fuels or as solvents for laquers, perfumes, and the like.

VIII. Examples

The batch reactions in the following examples were carried in Fischer-Porter aerosol compatibility bottles equipped with a pressure gauge and magnetic stirrer. Generally, the bottle was charged with the catalyst and the starting olefinic alcohol, sealed, flushed 5 times with hydrogen, and pressured to the desired pressure with hydrogen. The reaction mixture was heated to the desired reaction temperature in an oil bath. At the conclusion of the reaction time period, the bottle was cooled and vented. The reaction mixture was filtered to remove the catalyst and the filtrate was analyzed by gas-liquid chromatography (glc). Variations of this procedure will be noted in the examples.

The starting material was commercially available 3-methyl-3-buten-1-ol (Chemical Samples Company). The palladium on carbon (Pd/C) catalyst was a commercially available catalyst which contained 10 weight % Pd based on the support weight. The other supported catalysts were prepared by dissolving a metal compound (palladium nitrate or palladium chloride) in water, filtering, and depositing the metal compound on the finely divided (usually less than about 100 mesh) support in a rotary evaporator while slowly evaporating the water. The impregnated support was then reduced in a stream of hydrogen at 300°–350° C. for about 18 hours.

EXAMPLE I

A series of control runs was carried out utilizing the apparatus and procedure described above for the isomerization of 3-methyl-3-buten-1-ol. In each run, the reactor was charged with 10 g. of 3-methyl-3-buten-1-ol and the catalyst or support, if used. The initial hydrogen pressure was 3 psig and the reaction was carried out at 130° C. for 2 hours. Various catalysts and supported catalysts were used in these runs. The results of these runs are shown in Table I.

Table I

| Run[a] No. | Catalyst[b] Metal/Support | g. | Conversion,[c] wt. % | Selectivity[d] wt. % |
|---|---|---|---|---|
| 1 | none/none | — | 0.4 | 85 |
| 2 | Pd[e] | 0.025 | 2.6 | 63 |
| 3 | none/ThO$_2$[e] | 0.25 | 0.9 | 99 |
| 4 | Pd/C | 0.24 | 31 | 97 |
| 5 | Pd/C | 1.0 | 29 | 78 |
| 6 | Pd/ZnO | 0.5 | 0.7 | 96 |
| 7 | Pd/MgO | 0.5 | 34 | 89 |
| 8 | pd/La$_2$O$_3$ | 0.5 | 18 | 86 |
| 9 | PdCl$_2$/none | 0.25 | 73 | 16 |
| 10 | (C$_6$H$_5$CN)$_2$PdCl$_2$/none | 0.1 | 34 | 10 |

[a]Each run was at 130° C. for 2 hours with an initial hydrogen pressure of 3 psig.
[b]The Pd/C catalyst contained 10 weight % Pd and the other supported catalysts contained about 3 weight % Pd with all % being based on the support weight.
[c]Conversion of 3-methyl-3-buten-1-ol.
[d]Selectivity to 3-methyl-2-buten-1-ol based on the amount of 3-methyl-3-buten-1-ol converted.
[e]Very finely divided powder.

The results of Table I show that a very low conversion of 3-methyl-3-buten-1-ol occurs in the absence of an isomerization catalyst (run 1), in the presence of unsupported palladium metal (run 2), or in the presence of thorium oxide (run 3). Several runs (runs 4 to 8) using various supported palladium catalysts gave conversions as high as 34 weight % within the reaction time of two hours. Runs 9 and 10 utilized palladium compounds as catalysts and although conversions of 73 and 34 weight % were achieved, the selectivities to 3-methyl-2-buten-1-ol were very low.

EXAMPLE II

A series of invention runs were carried out utilizing various quantities of palladium on thorium oxide catalysts which contained 2.4 to 3 weight % palladium based on the weight of the support. The apparatus and procedure in each run was as described previously. In each run, the reactor was charged with 3-methyl-3-buten-1-ol (10 g.) and the catalyst. The initial hydrogen pressure was 3 psig and the runs were carried out at 130° C., for 2 hours. The results of these runs are shown in Table II.

Table II

| Run[a] No. | Catalyst,[b] g. | Conversion,[c] wt. % | Selectivity,[d] wt. % |
|---|---|---|---|
| 11 | 0.1 | 39 | 99 |
| 12 | 0.25 | 44 | 95 |
| 13 | 0.25 | 52 | 90 |
| 14 | 0.5 | 41 | 86 |
| 15 | 0.5 | 47 | 93 |
| 16 | 0.5 | 54 | 99 |
| 17 | 1.0 | 52 | 82 |

[a]Each run was 130° C. for 2 hours.
[b]The catalysts contained 2.4 to 3 wt. % Pd based on the weight of the support.
[c]Conversion of 3-methyl-3-buten-1-ol.
[d]Selectivity to 3-methyl-2-buten-1-ol based on the amount of 3-methyl-3-buten-1-ol converted.

The results of runs 11 through 17 show that a Pd/ThO$_2$ catalyst isomerizes 3-methyl-3-buten-1-ol to 3-methyl-2-buten-1-ol in high conversion and high selectivity at a wide variety of catalyst levels. A comparison of the results of these runs with the results of runs in Example I shows that the isomerization process of this invention utilizing the Pd/ThO$_2$ catalyst provides significantly higher conversions then the prior art catalysts.

EXAMPLE III

Another series of isomerization runs was carried out with a Pd/ThO$_2$ catalyst. The apparatus and procedure described above was utilized except in runs 28 and 29 where other vapor phases above the reaction mixtures were used. In each run, the reaction vessel was charged with 10 g. of 3-methyl-3-buten-1-ol and the catalyst. The catalyst amounts, vapor phases, reaction temperatures, and reaction results are presented in Table III.

Table III

| Run[a] No. | Catalyst,[b] g. | Initial $H_2$ Press., psig. | Other Vapor Phase | Reaction Temp., °C. | Conversion,[c] Wt. % | Selectivity[d] Wt. % |
|---|---|---|---|---|---|---|
| 18 | 0.25 | 3 | — | 100 | 23 | 98 |
| 19 | 0.25 | 3 | — | 110 | 38 | 99 |
| 20 | 0.25 | 3 | — | 120 | 49 | 99 |
| 21 | 0.25 | 3 | — | 125 | 47 | 89 |
| 22 | 0.25 | 3 | — | 125 | 24 | 96 |
| 23 | 0.25 | 3 | — | 125 | 51 | 90 |
| 24 | 0.5 | 3 | — | 125 | 60 | 89 |
| 13 | 0.25 | 3 | — | 130 | 52 | 90 |
| 25 | 0.25 | 6 | — | 130 | 50 | 91 |
| 26 | 0.25 | 9 | — | 130 | 43 | 94 |
| 27 | 0.25 | 20 | — | 130 | 62 | 81 |
| 28 | 0.25 | — | Air | 130 | 3 | 31 |
| 29 | 0.25 | — | $N_2$ | 130 | 2 | 100 |

[a]Each run was carried out for 2 hours.
[b]See footnote (b) of Table II.
[c]See footnote (c) of Table II.
[d]See footnote (d) of Table II.

Invention runs 18 to 27 show that the isomerization reaction of this invention proceeds at a variety of isomerization temperatures and at a variety of initial hydrogen pressures. Runs 28 and 29 show that little isomerization occurs in the absence of hydrogen and in the presence of air or nitrogen.

EXAMPLE IV

An isomerization run (run 30) was carried out to demonstrate the catalytic isomerization of this invention at a low temperature. The reactor was charged with 100 g. of 3-methyl-3-buten-1-ol and 13 g. of a palladium on thorium oxide catalyst which contained 2.3 weight % palladium based on the weight of the support. The reactor was pressured to 34 psig with hydrogen and the reaction was carried out at 22° C. for 2 hours.

The glc analysis of the product mixture showed that 53 weight % of the 3-methyl-3-buten-1-ol had been converted and that the selectivity to 3-methyl-2-buten-1-ol based on the amount of 3-methyl-3-buten-1-ol converted was 94 weight %. These results demonstrate the use of the process of this invention for the isomerization of 3-methyl-3-buten-1-ol with good conversion and high selectivity to 3-methyl-2-buten-1-ol at 22° C.

EXAMPLE V

A control run (run 31) was carried out to demonstrate the isomerization of 3-methyl-3-buten-1-ol in the presence of the prior art catalyst at 22°. The reactor was charged with 10 g. of 3-methyl-3-buten-1-ol and 0.5 g. of a palladium on carbon catalyst which contained 10 weight % palladium based on the weight of the support. The reactor was pressured to 34 psig with hydrogen and the reaction was carried out at 22° C. for 2 hours.

The glc analysis of the reaction product mixture showed that 82% of the 3-methyl-3-buten-1-ol had been converted and that the selectivity to 3-methyl-2-buten-1-ol based on the amount of 3-methyl-3-buten-1-ol converted was 82%. Although the conversion is higher in this run than in Example IV, the selectivity is lower.

EXAMPLE VI

A series of runs was carried out to show the recovery and recycle of the isomerization catalyst of this invention. In run 32, the first run of this series, the reactor was charged with 10 g. of 3-methyl-3-buten-1-ol and 5 g. of palladium on thorium oxide (3 weight % Pd based on the weight of the support). The reactor was pressured to 7 psig with hydrogen and the reaction was carried out at 130° C. for 2 hours. The reaction product was worked up and analyzed as described previously. The filtered catalyst was used in the next run along with enough fresh catalyst to bring the catalyst weight to 5 g. to makeup for catalyst losses in handling. This sequence of recovering the isomerization catalyst from a run and using it in the next run was continued through several runs. After run 40, the catalyst showed signs of having lower activity and was regenerated by treating the catalyst with hydrogen at 680° F. for 16 hours. The regenerated catalyst was then used in run 41. The results of these runs are shown in Table IV.

Table IV

| | Run[a] No. | Conversion[b] Wt. % | Selectivity,[c] Wt. % |
|---|---|---|---|
| | 32 | 53 | 69 |
| | 33 | 56 | 78 |
| | 34 | 61 | 76 |
| | 35 | 59 | 78 |
| | 36 | 58 | 83 |
| | 37 | 54 | 82 |
| | 38 | 52 | 82 |
| | 39 | 50 | 80 |
| | 40 | 39 | 69 |
| Regeneration | | | |
| | 41 | 51 | 84 |
| | 42 | 46 | 94 |

[a]All runs were carried out at 130° C. for 2 hours.
[b]See footnote (c) of Table I.
[c]See footnote (d) of Table I.

The results shown in Table IV show that the isomerization catalyst of this invention can be recovered and recycled to another isomerization run. The catalyst maintained good physical stability and catalytic activity during the recycling and regeneration.

EXAMPLE VII

A run (run 43) was carried out to demonstrate the isomerization of 3-methyl-3-buten-1-ol by the process of this invention in a continuous reactor. The continuous reactor was a ¼" (6.4 mm)×18" (457 mm) tube fitted with an electric heater. The reactor was packed with 25 g. of a palladium on thorium oxide catalyst (3 weight % Pd based on the weight of the support). The 3-methyl-3-buten-1-ol was pressured to 20 psig with hydrogen and was passed upward through the reactor at a LHSV of 1.42. Samples were collected from the reactor effluent at regular intervals. The results of the glc analysis of several of the samples taken during run are shown in Table V.

Table V

| Effluent Sample No. | H₂ Pressure, psig | Conversion, % | Selectivity, % |
|---|---|---|---|
| 2 | 24 | 69 | 91 |
| 4 | 24 | 59 | 97 |
| 12 | 24 | 58 | 96 |
| 15 | 24 | 57 | 91 |
| 17 | 28 | 47 | 88 |
| 21 | 32 | 42 | 93 |
| 24 | 32 | 38 | 100 |
| 26 | 32 | 38 | 96 |

The results presented in Table V show that 3-methyl-3-buten-1-ol can be isomerized to 3-methyl-2-buten-1-ol in a continuous reactor in good conversion and selectivity. The conversion was decreasing in later samples in the run.

EXAMPLE VIII

Two batch runs were carried out which involved the isomerization of a mixture of 3-methyl-3-buten-1-ol (III) and 3-methyl-2-buten-1-ol (IV) which contains predominantly the IV isomer to yield a product mixture enriched in the III isomer. Each run started with a mixture which contained 98 weight % of III and IV and 98.6 weight % of the two isomers was IV and 1.4 weight % was III. Run 44 was a control run conducted in the absence of any added catalyst and used 4.24 g. of the above described mixture. Run 45 was an invention run which utilized 6.28 g. of the above described mixture and 2 g. of a Pd/ThO₂ catalyst (3 weight % Pd based on the support weight). Each run was carried out using the previously described apparatus and procedure at a reaction temperature of 130° C. and an initial hydrogen pressure of 7 psig for 2 hours.

In the reaction product mixture from control run 44, 95.7 weight % of the isomeric unsaturated alcohols was IV and 4.3 weight % was III. In the reaction product mixture from invention run 45 with a Pd/ThO₂ catalyst, 73 weight % of the isomeric unsaturated alcohols was IV and 27 weight % was III.

The results of these two runs show that the thermal isomerization of a mixture of III and IV which is predominantly IV is slow while the Pd/ThO₂ catalyzed isomerization results in a product mixture substantially enriched in the III isomer.

I claim:

1. An isomerization process which comprises contacting
    (a) at least one unsaturated alcohol represented by

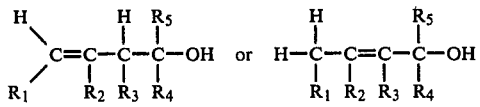

wherein each of $R_1$, $R_2$, $R_3$, $R_4$ and $R_5$ is selected from hydrogen, alkyl radicals having from 1 to 10 carbon atoms per molecule and aryl and substituted aryl radicals containing from 6 to 14 carbon atoms per molecule with the substituents being one or more or a mixture of alkyl or cycloalkyl groups containing 1 to 10 carbon atoms, or halogens, with
    (b) hydrogen in the presence of
    (c) a catalytically effective amount of a catalyst comprising palladium and thorium oxide under isomerization conditions which will form unsaturated isomers of said alcohols.

2. A process according to claim 1 wherein (c) is a catalyst containing from 0.1 to about 30 weight percent palladium and the balance thorium oxide and said isomerization conditions include a temperature in the range of about 0° to about 200° C. and a hydrogen pressure in the range of about 0 to about 100 psig.

3. A process according to claim 1 wherein said catalyst (c) upon becoming inactive for the isomerization reaction is regenerated by feeding with hydrogen at an elevated temperature for a period of time sufficient to restore catalyst activity then resuming isomerization.

4. A process according to claim 1 wherein the isomerization reaction mixture is separated to obtain (1) the desired isomer thus produced, and (2) unconverted, unsaturated reactant (a) which is recycled to said contacting for further isomerization.

5. An isomerization process which comprises contacting
    (a) 3-methyl-3-buten-1-ol with
    (b) hydrogen in the presence of
    (c) a catalytically effective amount of a catalyst comprising palladium and thorium oxide under isomerization conditions which will form 3-methyl-2-buten-1-ol.

6. A process according to claim 5 wherein (c) is a catalyst containing from 0.1 to about 30 weight percent palladium and the balance thorium oxide.

7. A process according to claim 5 wherein said isomerization conditions include a temperature in the range of about 0° to about 200° C. and a hydrogen pressure in the range of about 0 to about 100 psig.

8. A process according to claim 5 for the isomerization of 3-methyl-3-buten-1-ol wherein the isomerization reaction mixture is separated to obtain (1) the desired isomer 3-methyl-2-buten-1-ol, and (2) unconverted, unsaturated reactant 3-methyl-3-buten-1-ol which is recycled to said contacting for further isomerization.

9. A process according to claim 5 wherein said catalyst (c) upon becoming inactive for the isomerization reaction is regenerated by feeding with hydrogen at an elevated temperature for a period of time sufficient to restore catalyst activity then resuming isomerization.

* * * * *